(12) United States Patent
Jeong et al.

(10) Patent No.: US 12,062,212 B2
(45) Date of Patent: Aug. 13, 2024

(54) OPTICAL COHERENCE TOMOGRAPHY-BASED INTRAORAL SCANNER CALIBRATION DEVICE AND METHOD FOR OBTAINING CALIBRATION INFORMATION THROUGH FULL AREA SCAN

(71) Applicants: Huvitz Co., Ltd., Anyang-si (KR); Ossvis Co., Ltd., Anyang-si (KR)

(72) Inventors: Hyo Sang Jeong, Daegu (KR); Min Soo Cho, Seoul (KR); Weon Joon Lee, Anyang-si (KR)

(73) Assignees: Huvitz Co., Ltd., Anyang-si (KR); Ossvis Co., Ltd., Anyang-si (KR)

( * ) Notice: Subject to any disclaimer, the term of this patent is extended or adjusted under 35 U.S.C. 154(b) by 357 days.

(21) Appl. No.: 17/676,106

(22) Filed: Feb. 18, 2022

(65) Prior Publication Data

US 2022/0270292 A1 Aug. 25, 2022

(30) Foreign Application Priority Data

Feb. 19, 2021 (KR) .......................... 10-2021-0022386

(51) Int. Cl.
*A61B 5/00* (2006.01)
*A61B 1/00* (2006.01)
(Continued)

(52) U.S. Cl.
CPC ............ *G06T 7/80* (2017.01); *A61B 1/00057* (2013.01); *A61B 1/24* (2013.01); *A61B 5/0033* (2013.01); *A61B 5/0066* (2013.01); *A61B 5/0073* (2013.01); *A61B 5/0088* (2013.01); *G01B 9/02091* (2013.01); *H04N 23/60* (2023.01);
(Continued)

(58) Field of Classification Search
CPC ..... A61B 1/00057; A61B 1/24; A61B 5/0033; A61B 5/0066; A61B 5/0073; A61B 5/0088; A61B 2560/0223; A61B 2576/02; G01B 9/02072; G01B 9/02091; G06T 7/80;
(Continued)

(56) References Cited

U.S. PATENT DOCUMENTS 9,593,933 B2 3/2017 Egea et al.
2012/0274783 A1 11/2012 Ko et al.
2018/0333232 A1 11/2018 Lee

FOREIGN PATENT DOCUMENTS

KR 20140108759 A 9/2014
KR 20180126164 A 11/2018
WO 2020208543 A1 10/2020

OTHER PUBLICATIONS

European Extended Search Report for Application No. 22157847.9, mailed Jun. 30, 2022.
(Continued)

*Primary Examiner* — Mark R Gaworecki
(74) *Attorney, Agent, or Firm* — United One Law Group LLC; Kongsik Kim; Jhongwoo Peck

(57) ABSTRACT

The present inventive concept relates to an optical coherence tomography (OCT)-based intraoral scanner calibration device including: a light source; an optical coupler for splitting the path of light irradiated from the light source in first light and second light; a reference part for generating reference light from the first light split by the optical coupler; a sample part for generating measurement light from the second light split by the optical coupler; and a signal generator for generating an OCT image from the reference light and the measurement light.

1 Claim, 4 Drawing Sheets

(51) Int. Cl.
  *A61B 1/24*      (2006.01)
  *G01B 9/02*      (2022.01)
  *G01B 9/02091*   (2022.01)
  *G06T 7/80*      (2017.01)
  *H04N 23/60*     (2023.01)
  *G01B 9/02055*   (2022.01)

(52) U.S. Cl.
  CPC ... *A61B 2560/0223* (2013.01); *A61B 2576/02* (2013.01); *G01B 9/02072* (2013.04); *G06T 2207/10101* (2013.01); *G06T 2207/30036* (2013.01); *G06T 2207/30244* (2013.01)

(58) Field of Classification Search
  CPC . G06T 2207/10101; G06T 2207/30036; G06T 2207/30244; H04N 23/60
  See application file for complete search history.

(56) References Cited

OTHER PUBLICATIONS

Office Action for KR Application 10-2021-0022386 mailed May 4, 2022.

Zabic, Miroslav et al., "Wavefront sensorless adaptive optics for optical coherence tomography guided femtosecond laser surgery in the posterior eye", Progress in Biomedical Optics and Imaging, SPIE—International Society for Optical Engineering, Bellingham, WA, US, vol. 10886, Feb. 20, 2019 (Feb. 20, 2019), pp. 1088603-1088603.

OPTICAL COHERENCE TOMOGRAPHY-BASED INTRAORAL SCANNER CALIBRATION DEVICE AND METHOD FOR OBTAINING CALIBRATION INFORMATION THROUGH FULL AREA SCAN

CROSS REFERENCE TO RELATED APPLICATION

The present application claims the benefit of Korean Patent Application No. 10-2021-0022386 filed in the Korean Intellectual Property Office on Feb. 19, 2021, the entire contents of which are incorporated herein by reference.

BACKGROUND

Technical Field

The present disclosure relates to an optical coherence tomography (OCT)-based intraoral scanner calibration device for and a method for obtaining calibration information through full area scans, and more specifically, an optical coherence tomography-based intraoral scanner calibration device and a method for obtaining calibration information through full area scans that is capable of making use of an image sensor located on the front end of a calibration tip of the intraoral scanner to linearly scan the scan area of the intraoral scanner, based on the pixel information corresponding to the input voltages of the intraoral scanner.

Description of the Related Art

An OCT device is used to obtain images of an object in a contactless and noninvasive way, and OCT is an imaging technology that is studied so as to solve problems of human hazards, prices, and measurement resolution existing measuring equipment such as an X-ray computed tomography (CT) machine, an ultrasound imaging device, and a magnetic resonance imaging (MRI) device has had.

The OCT device obtains cross-section images in a micrometer unit through a Michelson interferometer and has the images with higher resolution than existing ultrasound images. Further, advantageously, the OCT device uses a near-infrared light source to measure the interior of an object in a non-invasive way, is possible to obtain real time OCT images, and can be made to a small-sized device and a low-priced device.

The conventional OCT device does not obtain different OCT images of an object continuously, and so as to obtain the different OCT images, accordingly, a plurality of optical couplers have to be used.

To solve such a problem, various calibration processes are needed. In conventional technologies, however, a target such as a lattice is used to require an image analysis process, and if the lattice is used, besides, it is hard to distinguish one area image from the other area image so that even though an error may occur, it cannot be checked easily.

SUMMARY

Accordingly, the present inventive concept has been made in view of the above-mentioned problems occurring in the related art, and it is an object of the present inventive concept to provide an OCT-based intraoral scanner calibration device and method that is capable of linearly calibrating non linear characteristics of an OCT-based intraoral scanner.

It is another object of the present inventive concept to provide a method for obtaining calibration information of input voltages of an OCT-based intraoral scanner for linearly scanning a scan area, based on scan position information at measurement sample positions on the full area of the input voltages of the scanner.

To accomplish the above-mentioned objects, according to one aspect of the present inventive concept, there is provided an optical coherence tomography (OCT)-based intraoral scanner calibration device including: a light source; an optical coupler for splitting the path of light irradiated from the light source in first light and second light; a reference part for generating reference light from the first light split by the optical coupler; a sample part for generating measurement light from the second light split by the optical coupler; and a signal generator for generating an OCT image from the reference light and the measurement light.

According to the present inventive concept, desirably, the sample part may include a calibration tip mounted on a probe tip and having an image sensor.

According to the present inventive concept, desirably, the image sensor may obtain pixel information on a full position area of a measurement object that corresponds to input voltages of an OCT intraoral scanner.

According to the present inventive concept, desirably, the obtained pixel information may correspond to the position values of the measurement object.

To accomplish the above-mentioned objects, according to another aspect of the present inventive concept, there is provided a method for obtaining calibrated information through full area scans using an optical coherence tomography (OCT)-based intraoral scanner by acquiring pixel information through the full area scans on an x-axis and a y-axis, by means of a calibration tip that is mounted a probe tip of the OCT-based intraoral scanner and has an image sensor, and by transforming position information compared to input voltages corresponding to the acquired pixel information into the input voltages compared to the position information, the method including the steps of: increasing a y-axis input voltage by one step voltage value from an initial value (Vy=Vmin); whenever the y-axis input voltage is increased by one step voltage value from the initial value, increasing an x-axis input voltage by one step voltage value from an initial value (Vx=Vmin) to store the position values of the image sensor generated until the x-axis input voltage is increased to a maximum input voltage; until the y-axis input voltage reaches the maximum voltage, repeatedly storing the position values of the x-axis full area voltages according to the y-axis input voltages; and transforming the stored position values of the x-axis full area voltages into the input voltages compared to the position information to thus obtain the calibrated voltage values according to the full area positions of the measurement object.

After the step of obtaining the calibrated voltage values according to the full area positions, desirably, the method may further include the steps of: generating voltage values to be inputted to micro-electromechanical systems (MEMS), based on the calibrated voltage values; generating a camera trigger signal at a position corresponding to the generated voltage inputs to the MEMS; inputting the voltage values to the MEMS; and outputting the camera trigger signal at the position corresponding to the voltage values inputted to the MEMS.

After the step of obtaining the calibrated voltage values according to the full area positions, desirably, the method may further include the steps of: generating a voltage waveform to operate the MEMS; inputting the generated voltage waveform to the MEMS; and if the voltage value inputted to the MEMS is the calibrated voltage value, inputting the trigger signal to a camera.

BRIEF DESCRIPTION OF THE DRAWINGS

The above and other objects, features and advantages of the present inventive concept will be apparent from the following detailed description of the preferred embodiments of the invention in conjunction with the accompanying drawings, in which.

DETAILED DESCRIPTION OF THE PREFERRED EMBODIMENTS

Objects, characteristics and advantages of the present inventive concept will be more clearly understood from the detailed description as will be described below and the attached drawings. Before the present inventive concept is disclosed and described, it is to be understood that the disclosed embodiments are merely exemplary of the invention, which can be embodied in various forms. An embodiment of the present inventive concept as will be discussed later will be in detail described so that it may be carried out easily by those having ordinary skill in the art, and therefore, this does not limit the idea and technical scope of the invention.

Hereinafter, the present inventive concept will be explained in detail with reference to the attached drawings.

Figure 1:
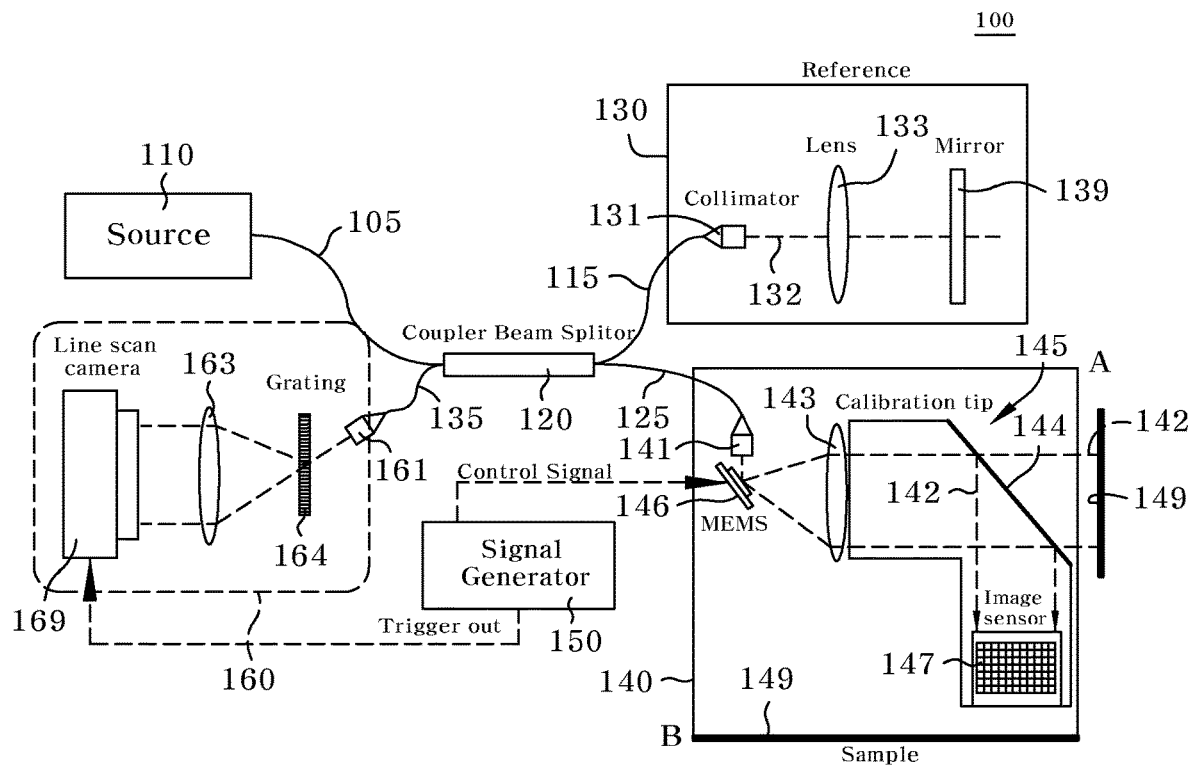
FIG. 1 is a concept view showing an OCT-based intraoral scanner on which a calibration tip is mounted, which is adopted in the present inventive concept.
Figure 2:
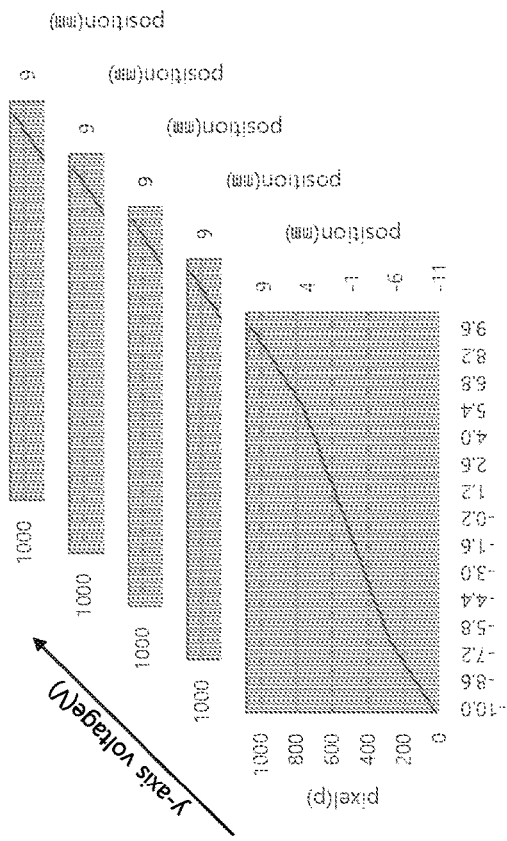
FIG. 2 is a graph showing the pixel information acquired through the calibration tip that corresponds to position information.
Figure 2:
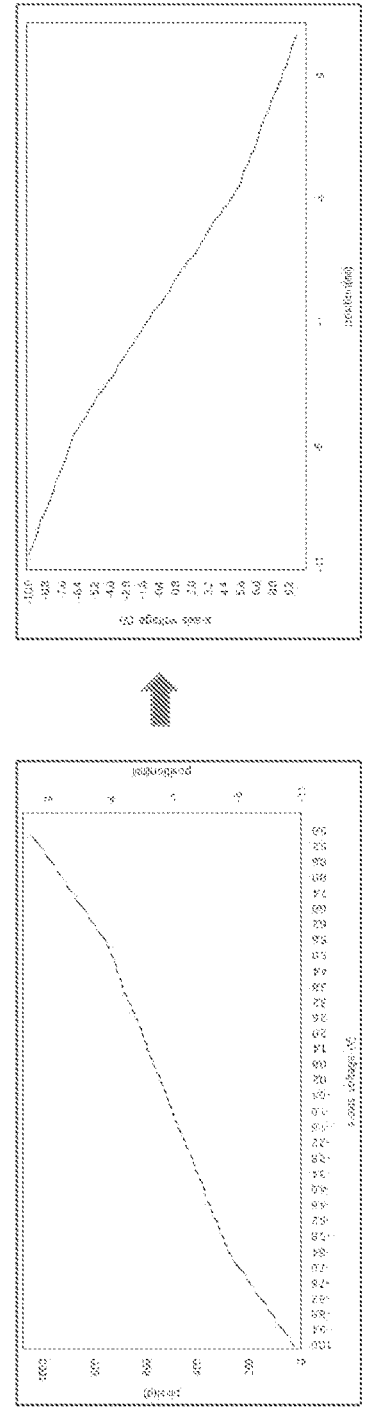

FIG. 1 is a concept view showing an OCT-based intraoral scanner on which a calibration tip 145 is mounted, which is adopted in the present inventive concept, and FIG. 2 is a graph showing the pixel information acquired through the calibration tip 145 that corresponds to position information.

Referring to FIGS. 1 and 2, an OCT-based intraoral scanner calibration device according to the present inventive concept includes a light source 110, an optical coupler or beam splitter 120 for splitting the path of light irradiated from the light source in first light and second light, a reference part 130 for generating reference light from the first light split by the optical coupler or beam splitter, a sample part 140 for generating measurement light from the second light split by the optical coupler or beam splitter 120, and a detector part 160 for generating an OCT image from the reference light and the measurement light.

The light source 110 generates light, and the light generated from the light source 110 is transmitted to the optical coupler or beam splitter 120 through optical fibers. The light source 110 emits light having a wavelength in a near-infrared region, but it is not limited necessarily thereto.

The optical coupler or beam splitter 120 splits the path of the incident light through the optical fibers from the light source 110 in the first light and the second light. The first light split through the optical coupler or beam splitter 120 is inputted to the path of the reference light, and the second light to the path of the measurement light.

According to an embodiment of the present inventive concept, the first light emitted from the optical coupler 120 is inputted to the reference part 130 through the optical fibers disposed between the optical coupler 120 and the reference part 130, and the second light to the sample part 140 through the optical fibers disposed between the optical coupler 120 and the sample part 140. The sample part 140 has a probe tip mounted thereon to capture the teeth scan in the oral cavity.

The reference light is generated from the first light inputted to the reference part 130, and the measurement light from the second light inputted to the sample part 140. The reference light, which moves by a given path in the reference part 130 and is reflected and outputted therefrom, is inputted again to the optical coupler 120 through the optical fibers. The measurement light, which moves by a given path in the sample part 140, is reflected onto a measurement object, and is outputted therefrom, is inputted again to the optical coupler 120 through the optical fibers.

The reference light and the measurement light, which are incident onto the optical coupler 120 through the optical fibers from the reference part 130 and the sample part 140, are inputted to the detector part 160 through the optical fibers.

The detector part 160 generates the OCT images for the measurement object from the combined reference light and measurement light.

According to the present inventive concept, in specific, the sample part 140 has a calibration tip 145 mounted on the probe tip and having an image sensor 147.

The image sensor 147 is scanned with a measurement light of the OCT-based intraoral scanner by changing input voltages for controlling the OCT-based intraoral scanner, thereby, a full area scan of the OCT-based intraoral scanner is performed on the image sensor 147. The image sensor 147 of the calibration tip 145 obtains pixel information corresponding to full area input voltages, as scanner input voltages. The pixel information corresponds to the position information of the measurement object, i.e., the scanning position of the measurement light.

As there is a given distance per one pixel, that is, the position information of the measurement object can be acquired from the pixel information obtained from the image sensor 147. According to the present inventive concept, therefore, the pixel information corresponding to the input voltages is the position information of the measurement object (See FIG. 2).

Further, the input voltages to the obtained position information are transformed into the position information to input voltages to obtain the input voltages at the calibrated positions through full area scans (See FIG. 2). Namely, from the acquired pixel information (position) and the input voltages for acquired the pixel information, a calibrated input voltage with respect to a position scanned with the measurement light is obtained.

Figure 3:
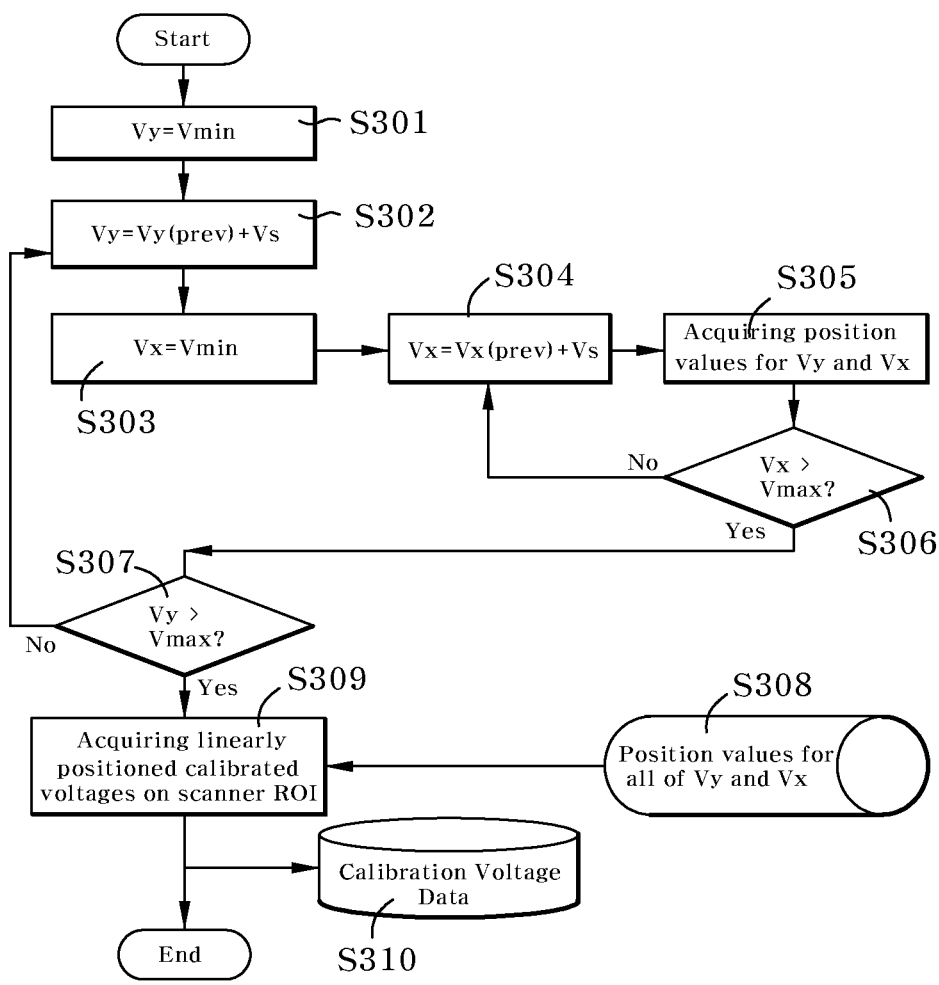
FIG. 3 is a flowchart showing a process of obtaining calibrated input voltages through full area scans according to the present inventive concept.

FIG. 3 is a flowchart showing a process of obtaining calibrated input voltages through full area scans according to the present inventive concept.

Referring to FIG. 3, first, a y-axis input voltage is increased by one step voltage value from an initial value (Vy=Vmin).

In this case, whenever the y-axis input voltage is increased by one step voltage value from the initial value, an x-axis input voltage is increased by one step voltage value from an initial value (Vx=Vmin), and accordingly, the position values of the image sensor, which are generated until the x-axis input voltage is increased from a minimal input voltage to a maximum input voltage, are stored. This is because the pixel values measured by the image sensor correspond to the position values.

Next, the y-axis input voltage is increased again by one step voltage value, and in this case, the position values of the image sensor, which are generated until the x-axis input voltage is increased from a minimal input voltage to a maximum input voltage, are stored.

Until the y-axis input voltage reaches the maximum voltage, the position values of the x-axis full area voltages according to the y-axis input voltages are repeatedly stored.

Through the repetition, the position information for all of Vx and Vy can be obtained, and the position information is transformed into input voltages compared to the position information to thus obtain linear position calibration voltages on a region of interest (ROI), that is, voltage information calibrated according to the positions of the measurement object (See FIG. 2).

Further, it is possible to capture the oral scan calibrated through the linear position calibration voltages obtained by the above-mentioned method.

Figure 4:
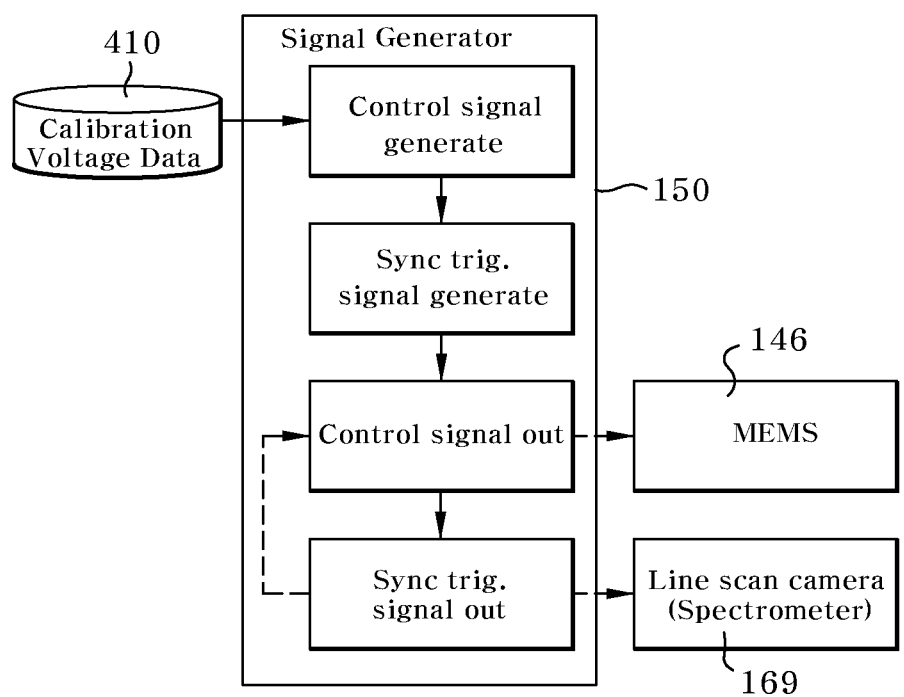
FIG. 4 is a flowchart showing a method for capturing linearly calibrated intraoral scans with the use of calibrated input voltages as the input voltages of the OCT-based intraoral scanner.

FIG. 4 is a flowchart showing a method for capturing the calibrated oral scan according to the present inventive concept.

Referring to FIG. 4, voltage values (Vx and Vy values) to be inputted to micro-electromechanical systems (MEMS) are generated based on the calibrated voltage values.

A camera trigger signal is generated at a position corresponding to the generated voltage inputs to the MEMS.

Next, the voltage values are inputted to the MEMS, and the camera trigger signal is outputted at the position corresponding to the voltage values inputted to the MEMS.

Through the above-mentioned process, the calibrated input voltages are used as the input voltages of the OCT-based intraoral scanner, thereby making it possible to capture the linearly calibrated oral scan.

Figure 5:
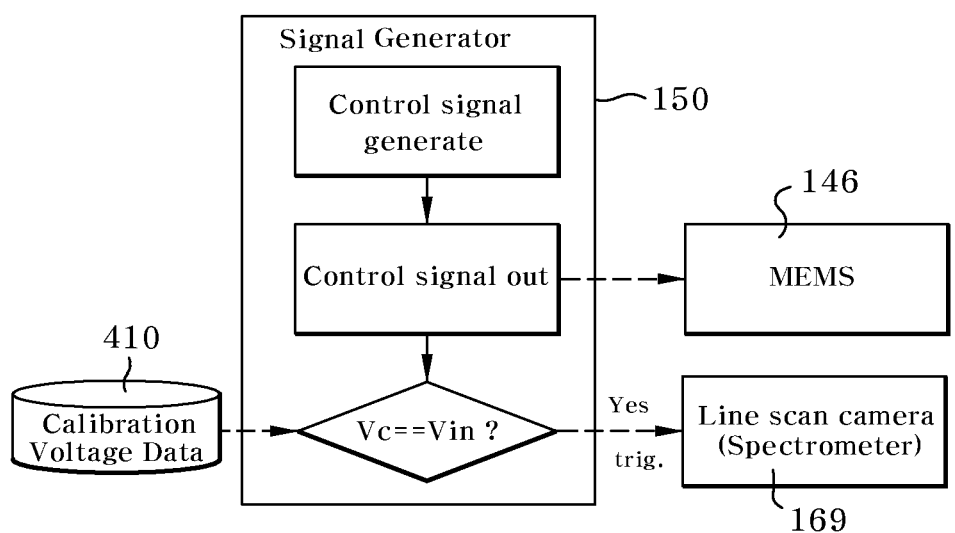
FIG. 5 is a flowchart showing another method for capturing linearly calibrated intraoral scans according to the present inventive concept.

FIG. 5 is a flowchart showing another method for capturing linearly calibrated intraoral scans according to the present inventive concept.

Referring to FIG. 5, first, a voltage waveform is generated to operate the MEMS, and next, the generated voltage waveform is inputted to the MEMS. In this case, if the voltage value inputted to the MEMS is the calibrated voltage value, the trigger signal is inputted to a camera.

Accordingly, a voltage of a sine wave or sawtooth wave is used as an input voltage for the OCT scanner, and if a current voltage corresponds to the calibrated input voltage, the trigger signal is generated to allow the camera to capture the linearly calibrated oral scan.

As set forth in the foregoing, the present inventive concept allows the pixel information of the image sensor to correspond to the position information, is intuitive so that calibration is easily performed, and replaces the input signal with the calibrated signal so that the calibration result can be conveniently checked.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above teachings. It is therefore intended that the scope of the invention be limited not by this detailed description, but rather by the claims appended hereto.

What is claimed is:

1. An optical coherence tomography (OCT)-based intraoral scanner calibration device comprising:
   a light source;
   an optical coupler for splitting the path of light irradiated from the light source into first light and second light;
   a reference part for generating reference light from the first light split by the optical coupler;
   a sample part for generating measurement light from the second light split by the optical coupler; and
   a detector part for generating an OCT image from the reference light and the measurement light,
   wherein the sample part comprises a calibration tip mounted on a probe tip and having an image sensor,
   wherein the image sensor is configured to be scanned with the measurement light of the OCT-based intraoral scanner by changing input voltages for controlling the OCT-based intraoral scanner, and thereby a full area scan of the OCT-based intraoral scanner with the measurement light is performed on the image sensor,
   wherein pixel information acquired from the image sensor which is scanned in accordance with the input voltages during the full area scan corresponds to the scanning position of the measurement light, and
   wherein the acquired pixel information and the input voltages provide a calibrated input voltage with respect to a position scanned with the measurement light.

* * * * *